United States Patent [19]
Kubo et al.

[11] Patent Number: 5,830,963
[45] Date of Patent: Nov. 3, 1998

[54] FLUORINE-CONTAINING MALEATE, FLUORINE-CONTAINING FUMARATE, FLUORINE-CONTAINING COPOLYMER AND STAINPROOFING AGENT

[75] Inventors: Motonobu Kubo; Takashi Enomoto; Mitsuhiro Usugaya; Taro Sano, all of Osaka, Japan

[73] Assignee: Daikin Industries Ltd., Osaka, Japan

[21] Appl. No.: 776,917

[22] PCT Filed: May 15, 1995

[86] PCT No.: PCT/JP95/00918

§ 371 Date: Feb. 13, 1997

§ 102(e) Date: Feb. 13, 1997

[87] PCT Pub. No.: WO96/05237

PCT Pub. Date: Feb. 22, 1996

[30] Foreign Application Priority Data

Aug. 15, 1994 [JP] Japan ..................... 6-191462

[51] Int. Cl.$^6$ .................................. C08F 18/20
[52] U.S. Cl. ........................... 526/245; 526/245
[58] Field of Search ............................. 526/245

[56] References Cited

U.S. PATENT DOCUMENTS

| | | | |
|---|---|---|---|
| 3,358,013 | 12/1967 | Freeman et al. | 526/245 |
| 3,438,946 | 4/1969 | Lichstein et al. | 526/245 |
| 3,594,353 | 7/1971 | Domba . | |
| 3,671,574 | 6/1972 | Knell et al. | 526/245 |
| 5,250,583 | 10/1993 | Kawaguchi et al. . | |
| 5,391,591 | 2/1995 | Kawaguchi et al. . | |

FOREIGN PATENT DOCUMENTS

| | | | |
|---|---|---|---|
| 0408917 | 1/1991 | European Pat. Off. | 526/245 |
| 48-8606 | 3/1973 | Japan . | |
| 51-37670 | 10/1976 | Japan . | |
| 63-55410 | 3/1988 | Japan | 526/245 |
| 5-105723 | 4/1993 | Japan . | |

OTHER PUBLICATIONS

Answer 5 of 5, 1985: 97050 doc. No. 102: 97050—Dainippon JP82–227078, 82, 12, 27—Abstract (in–house) pp. 13–16.

*Primary Examiner*—Joseph L. Schofer
*Assistant Examiner*—N. Sarofim

[57] ABSTRACT

(1) A perfluoroalkyl diester of maleic acid or fumaric acid,
(2) a copolymer obtained by polymerizing the perfluoroalkyl ester, a lower alkyl (meth)acrylate and, if necessary, styrene, and
(3) a stainproofing agent comprising the copolymer give excellent water repellency, oil repellency and stainproof properties which have never been heretofore obtained.

6 Claims, 2 Drawing Sheets

FLUORINE-CONTAINING MALEATE, FLUORINE-CONTAINING FUMARATE, FLUORINE-CONTAINING COPOLYMER AND STAINPROOFING AGENT

FIELD OF THE INVENTION

The present invention relates to a fluorine-containing maleate, a fluorine-containing fumarate, a fluorine-containing copolymer and a stainproofing agent.

RELATED ART

In order to impart water- and oil-repellency and stainproof properties to textile products (e.g. carpet, etc.), various stainproofing agents have hitherto been suggested.

Japanese Patent Kokoku Publication No. 8606/1973 discloses that stainproof properties are imparted by treating a fabric with a homopolymer obtained by polymerizing an ester of an unsaturated carboxylic acid having a perfluoroalkyl group at both ends. However, this homopolymer is insufficient in stainproof properties.

Japanese Patent Kokoku Publication No. 37670/1976 discloses that stainproof properties are imparted to fibers by treating the fibers with a polymer obtained by polymerizing (i) an ester of maleic or fumaric acid having a perfluoroalkyl group at one end and an aliphatic or aromatic group having no fluorine atom at the other end with (ii) the other polymerizable unsaturated compound. Since one end of the ester of maleic or fumaric acid has no fluorine atom, its polymerizablity is good. However, this polymer is insufficient in water- and oil-repellency and is also insufficient in stainproof properties.

U.S. Pat. No. 3,594,353 discloses that a water repellency and stainproof properties to oil are imparted to fibers by treating the fibers with a polymer obtained by homopolymerizing an ester of itaconic acid having a perfluoroalkyl group at both ends or one end or copolymerizing said ester with the other polymerizable unsaturated compound. However, this polymer is insufficient in water- and oil-repellency and stainproof properties.

Japanese Patent Kokai Publication No. 105723/1993 discloses that a water- and oil-repellency is imparted to fibers by treating the fibers with a polymer obtained by copolymerizing a fumarate ester having a bulky branched alkyl group at one end and a perfluoroalkyl group at the other end with the other copolymerizable unsaturated compound. However, this copolymer is insufficient in water- and oil-repellency and stainproof properties.

None of stainproofing agents which have hitherto been proposed presently has sufficient water- and oil-repellency and stainproof properties.

SUMMARY OF THE INVENTION

A first object of the present invention is to provide a stainproofing agent having sufficient water- and oil-repellency and stainproof properties.

A second object of the present invention is to provide a polymer constituting the stainproofing agent.

A third object of the present invention is to provide a monomer which affords said polymer.

The present invention provides a stainproofing agent comprising a fluorine-containing copolymer, in which said fluorine-containing copolymer comprises:

(A) at least one repeating unit derived from a monomer which is selected from the group consisting of an OH— and fluorine-containing maleate represented by the formula:

[wherein Rf is a perfluoroalkyl group having 3 to 21 carbon atoms], an OH— and fluorine-containing fumarate represented by the formula:

[wherein Rf is a perfluoroalkyl group having 3 to 21 carbon atoms], a fluorine-containing maleate represented by the formula:

[wherein Rf is a perfluoroalkyl group having 3 to 21 carbon atoms, and A is an alkylene group having 1 to 4 carbon atoms or (wherein $R^1$ is a hydrogen atom or an alkyl group having 1 to 4 carbon atoms, and $R^2$ is an alkylene group having 1 to 4 carbon atoms)], and a fluorine-containing fumarate represented by the formula:

[wherein Rf is a perfluoroalkyl group having 3 to 21 carbon atoms, and A is an alkylene group having 1 to 4 carbon atoms or (wherein $R^1$ is a hydrogen atom or an alkyl group having 1 to 4 carbon atoms, and $R^2$ is an alkylene group having 1 to 4 carbon atoms)], and (B) at least one repeating unit derived from an alkyl (meth)acrylate whose alkyl group has 1 to 6 carbon atoms. (Meth)acrylate means acrylate or methacrylate.

DETAILED DESCRIPTION OF THE INVENTION

In the copolymer of the present invention, the repeating unit (A) may be the above fluorine-containing maleate or fumarate which has an OH group or no OH group. It is preferred that the repeating unit (A) has the OH group. The reason why it is preferred to have the OH group is not clear, but it is assumed that properties of adhesion to a substrate are improved by having the OH group, thereby improving the stainproof properties and oil repellency.

The present invention provides a stainproofing agent comprising a fluorine-containing copolymer, said fluorine-containing copolymer comprising:

(A) at least one repeating unit derived from an OH— and fluorine-containing maleate represented by the formula:

$$\underset{H}{\overset{H}{\underset{\|}{\overset{C}{\underset{C}{\|}}}}}\underset{\underset{O}{\|}}{\overset{\overset{O}{\|}}{C}}-O-CH_2CHCH_2-Rf \atop \underset{OH}{|} \quad (I)$$

[wherein Rf is a perfluoroalkyl group having 3 to 21 carbon atoms], or a fluorine-containing maleate represented by the formula:

$$\underset{H}{\overset{H}{\underset{\|}{\overset{C}{\underset{C}{\|}}}}}\underset{\underset{O}{\|}}{\overset{\overset{O}{\|}}{C}}-O-A-Rf \quad (III)$$

[wherein Rf is a perfluoroalkyl group having 3 to 21 carbon atoms, and A is an alkylene group having 1 to 4 carbon atoms or $$-R^2-\underset{\underset{}{|}}{\overset{R^1}{N}}-\underset{\underset{O}{\|}}{\overset{\overset{O}{\|}}{S}}-$$

(wherein $R^1$ is a hydrogen atom or an alkyl group having 1 to 4 carbon atoms, and $R^2$ is an alkylene group having 1 to 4 carbon atoms)], (B) at least one repeating unit derived from an alkyl (meth)acrylate whose alkyl group has 1 to 6 carbon atoms, and (C) a repeating unit derived from styrene.

The present invention provides a stainproofing agent comprising a fluorine-containing copolymer, said fluorine-containing copolymer comprising:

(A) at least one repeating unit derived from an OH— and fluorine-containing fumarate represented by the formula:

$$\underset{Rf-CH_2CHCH_2O-\underset{\underset{OH}{|}}{\overset{}{C}}}{\overset{\overset{O}{\|}}{C}}\underset{\underset{C}{\|}}{\overset{C}{\|}}\underset{H}{\overset{OH}{\underset{|}{C-O-CH_2CHCH_2-Rf}}} \quad (II)$$

[wherein Rf is a perfluoroalkyl group having 3 to 21 carbon atoms], or a fluorine-containing fumarate represented by the formula:

$$\underset{Rf-A-O-\underset{\underset{O}{\|}}{\overset{}{C}}}{\overset{\overset{O}{\|}}{C-O-A-Rf}}\underset{\underset{C}{\|}}{\overset{C}{\|}}H \quad (IV)$$

[wherein Rf is a perfluoroalkyl group having 3 to 21 carbon atoms, and A is an alkylene group having 1 to 4 carbon atoms or $$-R^2-\underset{\underset{}{|}}{\overset{R^1}{N}}-\underset{\underset{O}{\|}}{\overset{\overset{O}{\|}}{S}}-$$

(wherein $R^1$ is a hydrogen atom or an alkyl group having 1 to 4 carbon atoms, and $R^2$ is an alkylene group having 1 to 4 carbon atoms)], (B) at least one repeating unit derived from an alkyl (meth)acrylate whose alkyl group has 1 to 6 carbon atoms, and (C) a repeating unit derived from styrene.

In the present invention, it is preferred that the repeating unit (A) is an OH— and fluorine-containing maleate represented by the formula:

$$\underset{H}{\overset{H}{\underset{\|}{\overset{C}{\underset{C}{\|}}}}}\underset{\underset{O}{\|}}{\overset{\overset{O}{\|}}{C}}-O-CH_2CHCH_2-Rf \atop \underset{OH}{|} \quad (I)$$

[wherein Rf is a perfluoroalkyl group having 3 to 21 carbon atoms], or an OH— and fluorine-containing fumarate represented by the formula:

$$\underset{Rf-CH_2CHCH_2O-\underset{\underset{OH}{|}}{\overset{}{C}}}{\overset{\overset{O}{\|}}{C}}\underset{\underset{C}{\|}}{\overset{C}{\|}}\underset{H}{\overset{OH}{\underset{|}{C-O-CH_2CHCH_2-Rf}}} \quad (II)$$

[wherein Rf is a perfluoroalkyl group having 3 to 21 carbon atoms]. The reason why it is preferred to have the OH group is not clear, but it is assumed that properties of adhesion to a substrate are improved by having the OH group, thereby improving the stainproof properties and oil repellency.

The present invention provides an OH— and fluorine-containing maleate represented by the formula:

(I)

[wherein Rf is a perfluoroalkyl group having 3 to 21 carbon atoms], and an OH— and fluorine-containing fumarate represented by the formula:

(II)

[wherein Rf is a perfluoroalkyl group having 3 to 21 carbon atoms].

The present invention also provide a fluorine-containing copolymer having a molecular weight of 1000 to 1000000, comprising:

(A) a repeating unit derived from the above fluorine-containing maleate or fumarate which has an OH group or no OH group, and (B) at least one repeating unit derived from an alkyl (meth)acrylate whose alkyl group has 1 to 6 carbon atoms, a weight ratio of the repeating unit (A) to the repeating unit (B) being from 95:5 to 5:95.

The copolymer of the present invention is obtained by polymerizing (A) at least one monomer selected from the fluorine-containing monomers (I) to (IV) with (B) the alkyl (meth)acrylate whose alkyl group has 1 to 6 carbon atoms (hereinafter referred to as a "lower alkyl (meth)acrylate") and, if necessary, (C) styrene. The polymerization may be any one of a solution polymerization, an emulsion polymerization and a suspension polymerization.

A copolymer may have a repeating unit represented by the formula:

[wherein Rf and A are as defined above] by cleaving a carbon-carbon double bond in the monomer (A).

A repeating unit represented by the formula:

[wherein $R^{1'}$ is hydrogen or a methyl group, and $R^{2'}$ is an alkyl group having 1 to 6 carbon atoms] is derived by cleaving a carbon-carbon double bond in the monomer (B).

A repeating unit represented by the formula:

is derived by cleaving a carbon-carbon double bond in the monomer (C).

The monomer (A) has low solubility in a normal solvent because both ends have a perfluoroalkyl group, but the monomer (A) is soluble in lower alkyl (meth)acrylate (B) and styrene (C). A stable emulsion can be obtained by mixing a monomer (A), a lower alkyl (meth)acrylate (B) and, if necessary, styrene (C) to dissolve the monomer (A) and adding water and an emulsifier to emulsify the mixture (e.g. mechanical emulsification, etc.), followed by polymerizing. When using solvents in which the monomers (A) to (C) are soluble (e.g. ketone such as methyl ethyl ketone (MEK), etc.; succinic acid diester such as diethyl succinate, etc.; chlorine-containing organic solvent such as perchloroethylene, etc.; glycol ethers such as dipropyleneglycolmonomethyl ether, etc.; or glycols such as dipropylene glycol, etc.), the solution polymerization can be conducted.

The emulsion polymerization may be conducted by polymerizing a monomer in an aqueous medium in the presence of an emulsifier. The aqueous medium may be water alone, but an organic solvent (e.g. glycol such as dipropylene glycol, etc.; glycol ether such as dipropylene glycol monomethyl ether, etc.; ketone such as methyl ethyl ketone, etc.; or succinic acid diester such as diethyl succinate, etc.) may be contained in an amount of not more than 20% by weight. The emulsifier may be a cationic, anionic or nonionic emulsifier. Examples of the emulsifier include a cationic emulsifier such as stearyltrimethylammonium chloride, etc.; an anionic emulsifier such as sodium laurylsulfate, etc.; and a nonionic emulsifier such as polyoxyethylenealkylphenyl ether, etc. In order to initiate the polymerization, a polymerization initiator is used. Examples of the polymerization initiator include azobisisobutyronitrile, azobis(2-amidinopropane) dihydrochloride, ammonium persulfate, etc. The polymerization temperature is usually from 60° to 80° C. The polymerization time usually depends on the polymerization temperature, and is usually from 5 to 20 hours.

In the copolymer containing no styrene, the weight ratio of the monomer (A) to the alkyl (meth)acrylate having 1 to 6 carbon atoms (B) is usually from 95/5 to 5/95, preferably from 80/20 to 10/90, more preferably from 70/30 to 15/85, further preferably from 70/30 to 40/60. When the ratio of the monomer (A) is less than 5% by weight, the oil repellency is liable to be lowered. When the ratio of the monomer (B) is less than 5% by weight, the stainproof properties are liable to be lowered.

In the copolymer containing styrene, the weight ratio of the monomer (A)/the alkyl (meth)acrylate having 1 to 6 carbon atoms (B)/styrene (C) is usually from 95-5/balance (5 or more)/0-95, preferably 80-10/20-90/1-50, more preferably 70-15/30-85/1-35, further preferably from 65-30/30-65/1-35. When the ratio of the monomer (A) is less than 5% by weight, the oil repellency is liable to be lowered. When the ratio of the monomer (A) exceeds 95% by weight, the stainproof properties are liable to be lowered. In addition, when the ratio of styrene exceeds 95% by weight, the oil repellency and stainproof properties are liable to be lowered.

The number-average molecular weight (according to gel permeation chromatography (GPC)) of the copolymer of the present invention is usually from 1000 to 1000000, preferably from 50000 to 400000.

The fluorine-containing maleates or fumarates (I) to (IV) are diesters of maleic or fumaric acid. In the fluorine-containing maleates or fumarates (I) to (IV), the number of carbon atoms of a Rf group is preferably from 6 to 14. The Rf group may be in the branched or straight-chain form.

The fluorine-containing maleate represented by the formula (I) can be obtained by the following reaction scheme.

[wherein Rf is as defined above].

That is, maleic acid may be reacted with 3-perfluoroalkyl-1,2-epoxypropane. It is preferred that this reaction is conducted in a solution dissolved in a solvent in the presence of a catalyst. Examples of the catalyst include an ammonium salt (e.g. trimethylbenzylammonium chloride, etc.) and a tertiary amine (e.g. dimethylbenzylamine, etc.). Examples of the solvent include ketone (e.g. methyl ethyl ketone, methyl isobutyl ketone, etc.); succinic acid diester such as diethyl succinate, etc.; glycol ethers such as dipropylene glycol monomethyl ether, etc.; and glycols such as dipropylene glycol, etc. The reaction temperature is usually from 80° to 120° C. The reaction temperature may be the temperature at which the solvent is allowed to reflux. The reaction time depends on the reaction temperature, and is usually from 5 to 20 hours.

The fluorine-containing fumarate represented by the formula (II) can be produced by replacing maleic acid with fumaric acid in the process for producing the fluorine-containing maleate represented by the formula (I). That is, the fluorine-containing fumarate (II) can be obtained by reacting fumaric acid with 3-perfluoroalkyl-1,2-epoxypropane. The conditions for producing the fluorine-containing fumarate (II) are the same as those for producing the fluorine-containing maleate (I).

The fluorine-containing maleate represented by the formula (III) can be produced according to the following reaction scheme.

[wherein Rf and A are as defined above].

It is preferred that this reaction is conducted in a solution dissolved in a solvent in the presence of a catalyst. Examples of the catalyst include p-toluenesulfonic acid, sulfuric acid and the like. Examples of the solvent include benzene, toluene and the like. The reaction is usually conducted at the reflux temperature of the solvent. The reaction time depends on the reaction temperature, and is usually from 6 to 12 hours.

The fluorine-containing fumarate represented by the formula (IV) can be produced by replacing maleic acid with fumaric acid in the process for producing the fluorine-containing maleate represented by the formula (III). That is, the fluorine-containing fumarate (IV) can be obtained by reacting fumaric acid with perfluoroalkyl alcohol. The conditions for producing the fluorine-containing fumarate (IV) are the same as those for producing the fluorine-containing maleate (III).

When the A group in the fluorine-containing maleate (III) and fluorine-containing fumarate (IV) is an alkylene group, the alkylene group may be —$CH_2$—, —$CH_2CH_2$—, —$CH_2CH_2CH_2$—, —$CH_2CH_2CH_2CH_2$—, and the like.

In the lower alkyl (meth)acrylate (B), the number of carbon atoms of a lower alkyl group is preferably from 1 to 6. Examples of the lower alkyl group include methyl group, ethyl group, n-propyl group, iso-propyl group, n-butyl group, iso-butyl group, t-butyl group, n-pentyl group, cyclopentyl group, n-hexyl group, cyclohexyl group and the like.

The lower alkyl (meth)acrylate (B) used in the copolymer may be a mixture of methyl (meth)acrylate and a $C_2$–$C_6$ alkyl (meth)acrylate (e.g. ethyl (meth)acrylate, butyl (meth)acrylate, etc.).

One of the lower alkyl (meth)acrylates dissolves the monomer (A), but the solubility of the monomer (A) is further improved by using two of them. Specifically, a combination of methyl methacrylate (MMA) and ethyl methacrylate (EMA) is preferred.

The molar ratio of the methyl (meth)acrylate to the $C_2$–$C_6$ alkyl (meth)acrylate may be preferably from 100:0 to 0:100, more preferably from 80:20 to 50:50.

In the stainproofing agent of the present invention, it is also possible to copolymerize with the other polymerizable monomer. Examples of the other polymerizable monomer include vinyl acetate, vinyl chloride, vinylidene chloride, acrylic acid and an alkyl ester thereof, methacrylic acid and an alkyl ester thereof, vinyl alkyl ether, halogenated alkyl vinyl ether, vinyl alkyl ketone, butadiene, isoprene, chloroprene, benzyl acrylate, benzyl (meth)acrylate, maleic anhydride, acrylamide, methacrylamide, diacetonacrylamide, N-methylol acrylamide, N,N-dimethylaminoethyl acrylate, N,N-dimethylaminoethyl methacrylate, 3-chloro-2-hydroxypropyl methacrylate, glycidyl acrylate, glycidyl methacrylate, hydroxyethyl acrylate, hydroxyethyl methacrylate, blocked isocyanate group-containing (meth)acrylate, urethane linkage-containing poly (meth)acrylate and the like.

It is also possible to copolymerize with a perfluoroalkyl group-containing (meth)acrylate.

The stainproofing agent of the present invention comprises a copolymer and a medium. The medium may be any solvent such as water and organic solvent (e.g. alcohol, ester, ketone, glycol, glycol ethers, etc.). In the stainproofing agent, the amount of the copolymer is usually from 15 to 40% by weight.

The stainproofing agent of the present invention can be applied by any method according to the kind of the material to be treated. For example, there can be used a method of applying a copolymer on the surface of a material to be treated, using a known application procedure such as immersion, coating, etc., followed by drying. If necessary, the curing may be conducted by applying together with a suitable crosslinking agent. Furthermore, the stainproofing agent of the present invention may be mixed with the other polymer, e.g. polymethyl methacrylate/ethyl methacrylate (P-MMA/EMA) emulsion. Other water repellents, oil repellents, and additives such as insect repellents, flame retardants, antistatic agents, softeners, wrinkle inhibitors, etc. may be appropriately added. In case of immersion, the concentration of the copolymer in the immersion solution is normally from 0.05 to 10% by weight. In case of coating, the concentration of the copolymer in the coating solution is usually from 0.1 to 5% by weight.

The material to be treated with the stainproofing agent of the present invention is preferably a textile, and a carpet is particularly preferred. Examples of the textile include animal- or vegetable-origin natural fibers such as cotton, hemp, wool, silk, etc.; synthetic fibers such as polyamide, polyester, polyvinyl alcohol, polyacrylonitrile, polyvinyl chloride, polypropylene, etc.; semisynthetic fibers such as rayon, acetate, etc.; inorganic fibers such as glass fibers, carbon fibers, asbestos fibers, etc.; and a mixture of these fibers. The textile may be in any form such as a fiber, a yarn, a cloth and the like. When a carpet is treated with the stainproofing agent of the present invention, the carpet may be formed after treating fibers or yarns with the stainproofing agent. Alternatively, the formed carpet may be treated with the stainproofing agent. Examples of the material to be treated with the stainproofing agent of the present invention include glass, paper, wood, hide, fur, asbestos, brick, cement, metal and oxide, ceramic, plastic, coated surface and plaster, in addition to the textile.

PREFERRED EMBODIMENT OF THE INVENTION

The present invention will be illustrated by the following Examples which do not limit the present invention.

The stainproofing agents obtained in the Examples and Comparative Examples were evaluated as follows.

Each emulsion obtained in the Examples and Comparative Examples is diluted with water to prepare a solution containing a solid content of 3% by weight, which is a treating solution. This treating solution is spray-coated on a nylon loop-pile carpet fabric (non-backed product) so that a coating weight is 100 g/m$^2$, followed by drying with heating at 130° C. for 3 minutes. The treated carpet is subjected to tests of the water repellency, oil repellency and dry soiling stainproof properties.

1) Water repellency

The water repellency is determined by gently dropping small drops of an isopropyl alcohol/water mixed solution having the following composition on the surface of a carpet fabric and measuring a maximum content of isopropyl alcohol in the solution which maintains a shape of the drop after 3 minutes.

| Mixing composition (volume ratio, %) | |
| --- | --- |
| Isopropyl alcohol | Water |
| 50 | 50 |
| 40 | 60 |
| 30 | 70 |
| 20 | 80 |
| 10 | 90 |
| 0 | 100 |

2) Oil repellency

The oil repellency is determined according to AATCC-TM-118-1966 by dropping several drops (diameter: about 4 mm) of the following test solution on two positions of the surface of a test cloth, observing the penetration state of the drops after 30 seconds and measuring a maximum point of the oil repellency given by the test solution which does not penetrate.

| Oil repellency | Test solution | Surface tension (dyn/cm, 25° C.) |
| --- | --- | --- |
| 8 | n-Heptane | 20.0 |
| 7 | n-Octane | 21.8 |
| 6 | n-Decane | 23.5 |
| 5 | n-Dodecane | 25.0 |
| 4 | n-Tetradecane | 26.7 |
| 3 | n-Hexadecane | 27.3 |
| 2 | n-Hexadecane 35 by weight Nujol 65 by weight | 29.6 |
| 1 | Nujol | 31.2 |
| 0 | Inferior to 1 | — |

3) Stainproof properties

First, a carpet is contaminated with a dry soil having the following composition according to JIS L 1023-1992.

| Component | | Weight ratio (%) |
| --- | --- | --- |
| Peat moss | | 40 |
| Portland cement | (JIS R 5210) | 17 |
| White clay | (JIS K 8746) | 17 |
| Diatomaceous earth | (JIS K 8330) | 17 |
| Carbon black | (JIS K 5107) | 0.1 |
| Iron oxide (III) for ferrite | (JIS K 1462) | 0.15 |
| Nujol | | 8.75 |

After the excess dry soil on the surface is sucked with a cleaner, brightness of the surface is measured by a calorimeter and a staining degree is calculated onthe basis of the following equation, which is taken for evaluation of dry soil stainproof properties.

$$\text{Staining degree}(\%) = [(L_0 - L)/L_0] \times 100$$

(wherein $L_0$: brightness before contamination,

L: brightness after contamination).

Synthesis Example 1
(Synthesis of Rf(OH) maleate)

3-Perfluoroalkyl (a mixture wherein a molar ratio of $C_6F_{13}$, $C_8F_{17}$, $C_{10}F_{21}$, $C_{12}F_{25}$ and $C_{14}F_{29}$ (=Rf) is 2:50:30:15:3, average molecular weight: 528)-1,2-epoxypropane (317 g, 0.600 mol) was dissolved in 200 g of methyl ethyl ketone (MEK), followed by heating to 80° C. After maleic acid (35.4 g, 0.305 mol) was added and sufficiently dissolved, 2.2 g of trimethylbenzylammonium chloride was added as a catalyst. The reaction was conducted in a reflux state for 20 hours. Then, contents were poured into a large amount of methanol to obtain 321 g of a precipitate (Rf(OH) maleate) (yield: 92%).

Figure 1:
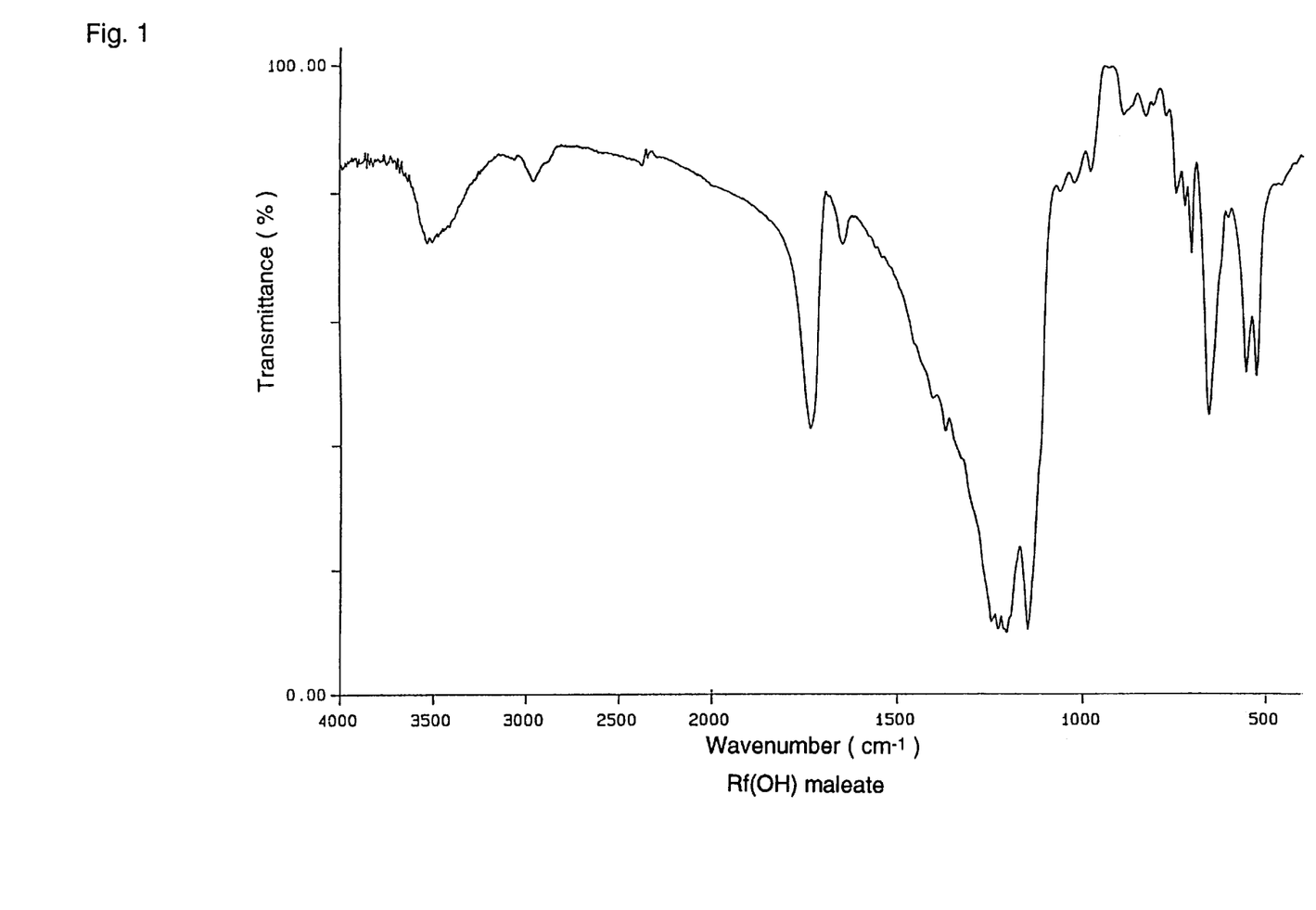
FIG. 1 is an IR chart of the product obtained in Synthesis Example 1.

It was confirmed by a mass spectrometry and a gas chromatography that a conversion of 3-perfluoroalkyl-1,2-epoxypropane is 100% and a new peak indicates bis-3-perfluoroalkyl-2-hydroxy-propyl maleate as a product. An IR chart of the product is shown in FIG. 1.

Synthesis Example 2
(Synthesis of Rf(OH) fumarate)

Figure 2:
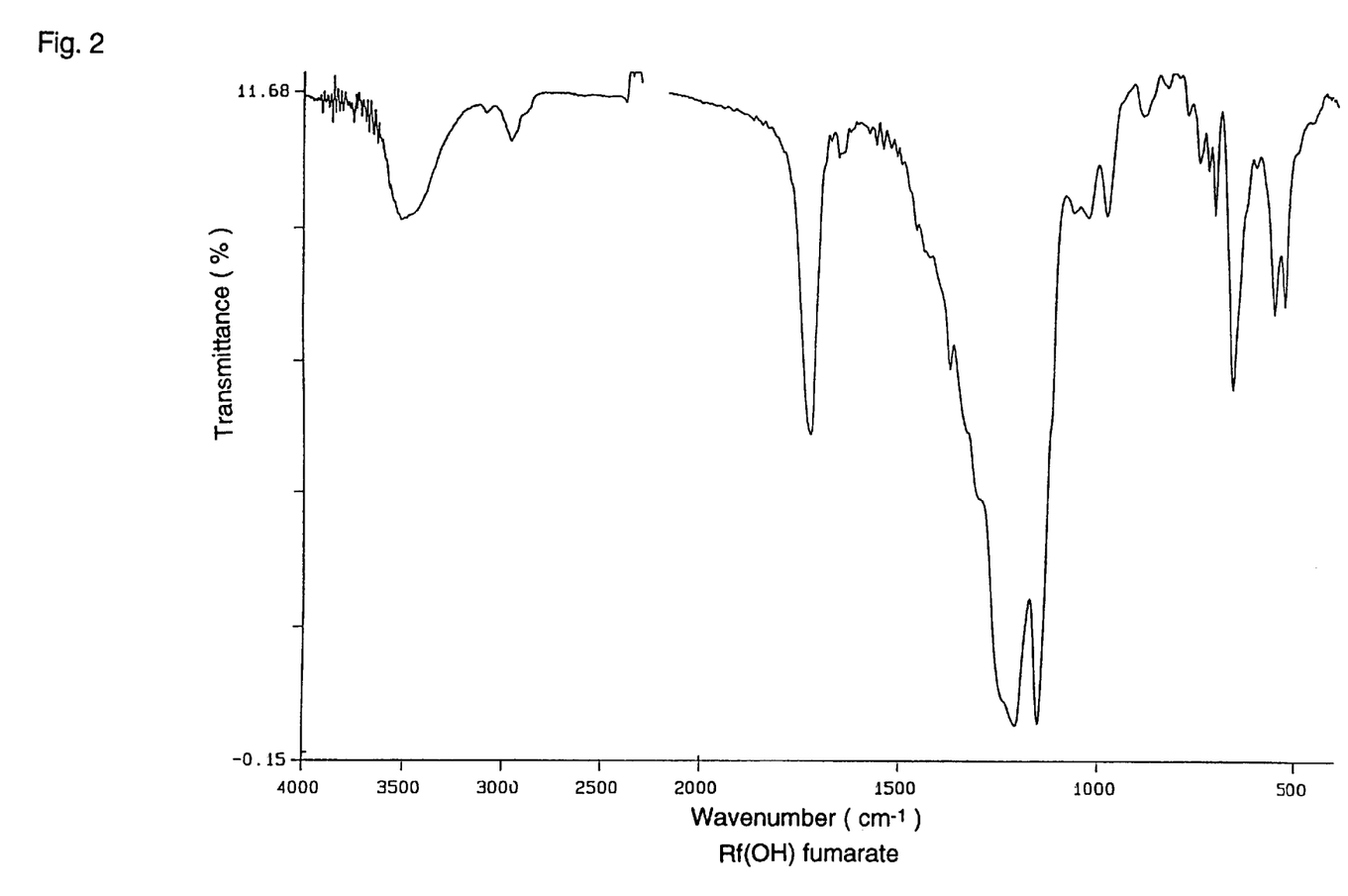
FIG. 2 is an IR chart of the product obtained in Synthesis Example 2.

The same manner as in Synthesis Example 1 was repeated, except for using 35.4 g of fumaric acid in place of maleic acid, to give a Rf(OH) fumarate. An IR chart of the product is shown in FIG. 2.

Synthesis Example 3
(Synthesis of Rf maleate)

This example illustrates the preparation of the fluorine-containing maleate (III) wherein A is —$CH_2CH_2$—.

Perfluoroalkylethanol [$RfCH_2CH_2OH$ (a mixture wherein a molar ratio of $C_6F_{13}$, $C_8F_{17}$, $C_{10}F_{21}$, $C_{12}F_{25}$ and $C_{14}F_{29}$ (=Rf) is 2:50:30:15:3, average molecular weight: 516)] (300 g, 0.581 mol), maleic acid (132 g, 1.138 mol) and 80 g of benzene were charged in a flask equipped with a dean-stalk trap, followed by heating to 55° C. with stirring. After 0.1 g of p-toluenesulfonioc acid and 0.4 g of sulfuric acid were added, and the mixture was heated to 83° C. The reaction was continuously conducted under reflux of benzene with removing water for 11 hours. After 28 g of an aqueous 10% sodium carbonate solution was added, the reaction solution was continuously stirred for 2 hours, and benzene and water were distilled off at 88° C. under 20 mmHg. The temperature was raised to about 90° C., an insoluble material was removed by filtering the solution through a SUS mesh to obtain 400 g of a Rf maleate (yield: 93%).

Synthesis Example 4
(Synthesis of Rf fumarate)

The same manner as in Synthesis Example 3 was repeated, except for using 132 g of fumaric acid in place of maleic acid, to prepare a fluorine- containing fumarate (IV) wherein A is —$CH_2CH_2$—.

EXAMPLE 1

120g of Rf(OH) maleate was sufficiently dissolved in 280 g of methyl methacrylate. Then 25 g of sodium α-olefinsulfonate, 28 g of Tween 80 (polyoxyethylenesorbitan monooleate), 0.1 g of laurylmercaptane and 684 g of deionized water were added and the mixture was emulsified using a high-pressure homogenizer. The resulting emulsion was charged in a 2 liter four-necked flask equipped with a reflux condenser, a nitrogen introducing tube, a thermometer and a stirring device, and then maintained at 60° C. under a nitrogen flow for about one hour. Ammonium persulfate (1.1 g) dissolved in 5 g of water was added to initiate the polymerization, followed by heating with stirring at 60° C. for 8 hours. The solid content of the resulting polymer emulsion was 40%.

The polymer has the composition shown in Table I.

The water repellency, oil repellency and stainproof properties were evaluated. The results are shown in Table I.

EXAMPLES 2 to 8

The same manner as in Example 1 was repeated, except for using the monomers shown in Table I, to prepare a copolymer. The copolymer has the composition shown in Table I.

The results of the water repellency, oil repellency and stainproof properties are shown in Table I.

EXAMPLES 9

120 g of Rf(OH) maleate was sufficiently dissolved in 120 g of methyl methacrylate, 120 g of ethyl methacrylate and 40 g of styrene. Then 28 g of sodium α-olefinsulfonate, 28 g of Tween 80 (polyoxyethylenesorbitan monooleate), 0.1 g of laurylmercaptane and 684 g of deionized water were added and the mixture was emulsified using a high-pressure homogenizer. The resulting emulsion was charged in a 2 liter four-necked flask equipped with a reflux condenser, a nitrogen introducing tube, a thermometer and a stirring device, and then maintained at 60° C. under a nitrogen flow for about one hour. Ammonium persulfate (1.1 g) dissolved in 5 g of water was added to initiate the polymerization, followed by heating with stirring at 60° C. for 8 hours. The solid content of the resulting polymer emulsion was 40%.

The polymer has the composition shown in Table I.

The results of the water repellency, oil repellency and stainproof properties are shown in Table I.

EXAMPLES 10 to 48 and Comparative Examples 1 to 16

The same manner as in Example 9 was repeated, except for using the monomers shown in Table I, to prepare a copolymer. The copolymer has the composition shown in Table I.

The results of the water repellency, oil repellency and stainproof properties are shown in Table I.

TABLE I

| Example No. | Composition of polymer (weight ratio) | Molecular weight (Mn) | Water repellency | Oil repellency | Stainproof properties |
|---|---|---|---|---|---|
| 1 | Rf maleate/MMA (30/70) | 250000 | 20 | 4 | 21 |
| 2 | Rf maleate/MMA/Sty (30/60/10) | 200000 | 20 | 5 | 19 |
| 3 | Rf maleate/MMA/EMA (30/35/35) | 160000 | 20 | 5 | 20 |
| 4 | Rf maleate/MMA/EMA/Sty | 160000 | 20 | 5 | 18 |

TABLE I-continued

|   | | | | | |
|---|---|---|---|---|---|
| 5 | Rf maleate/MMA/BMA/Sty (30/30/30/10) | 140000 | 20 | 5 | 19 |
| 6 | Rf (OH) maleate/MMA (30/70) | 150000 | 30 | 5 | 19 |
| 7 | Rf (OH) maleate/MMA/Sty (30/60/10) | 150000 | 30 | 6 | 17 |
| 8 | Rf (OH) maleate/MMA/EMA (30/35/35) | 150000 | 30 | 6 | 17 |
| 9 | Rf (OH) maleate/MMA/EMA/Sty (30/30/30/10) | 160000 | 30 | 6 | 15 |
| 10 | Rf (OH) maleate/MMA/BMA/Sty (30/30/30/10) | 160000 | 30 | 6 | 18 |
| 11 | Rf (OH) maleate/EMA (30/70) | 140000 | 30 | 5 | 20 |
| 12 | Rf (OH) maleate/EMA/Sty (30/35/35) | 160000 | 30 | 5 | 19 |
| 13 | Rf (OH) maleate/MMA/EMA (50/25/25) | 80000 | 30 | 5 | 18 |
| 14 | Rf (OH) maleate/MMA/EMA/Sty (50/20/20/10) | 80000 | 40 | 6 | 16 |
| 15 | Rf (OH) maleate/MMA/EMA (70/15/15) | 60000 | 40 | 6 | 19 |
| 16 | Rf (OH) maleate/MMA/EMA/Sty (70/12.5/12.5/5) | 60000 | 40 | 6 | 19 |
| 17 | Rf fumarate/MMA (30/70) | 300000 | 20 | 4 | 25 |
| 18 | Rf fumarate/MMA/Sty (30/60/10) | 350000 | 20 | 4 | 23 |
| 19 | Rf fumarate/MMA/EMA (30/35/35) | 170000 | 20 | 4 | 24 |
| 20 | Rf fumarate/MMA/EMA/Sty (30/30/30/10) | 190000 | 20 | 4 | 22 |
| 21 | Rf fumarate/MMA/BMA/Sty (30/30/30/10) | 170000 | 20 | 4 | 23 |
| 22 | Rf (OH) fumarate/MMA(30/70) | 170000 | 20 | 5 | 21 |
| 23 | Rf (OH) fumarate/MMA/Sty (30/60/10) | 180000 | 20 | 5 | 20 |
| 24 | Rf (OH) fumarate/MMN/EMA (30/35/35) | 170000 | 20 | 5 | 20 |
| 25 | Rf (OH) fumarate/MMN/EMA/Sty (30/30/30/10) | 180000 | 20 | 5 | 18 |
| 26 | Rf (OH) fumarate/MMA/BMA/Sty (30/30/30/10) | 180000 | 20 | 5 | 19 |
| 27 | Rf (OH) fumarate/MMA/EMA (50/25/25) | 100000 | 20 | 5 | 20 |
| 28 | Rf (OH) fumarate/MMA/EMA/Sty (50/20/20/10) | 100000 | 20 | 5 | 18 |
| 29 | Rf (OH) fumarate/MMA/EMA (70/15/15) | 60000 | 20 | 5 | 19 |
| 30 | Rf (OH) fumarate/MMA/EMA/Sty (70/12.5/12.5/5) | 60000 | 20 | 5 | 18 |
| 31 | Rf (OH) maleate/MMA/StA/ (30/60/10) | 140000 | 30 | 6 | 19 |
| 32 | Rf (OH) maleate/MMA/EMA/StA (30/30/30/10) | 140000 | 30 | 6 | 20 |
| 33 | Rf (OH) maleate/MA (30/70) | 200000 | 30 | 5 | 19 |
| 34 | Rf (OH) maleate/MA/EA (30/35/35) | 200000 | 30 | 5 | 19 |
| 35 | Rf (OH) maleate/MMA/EA (30/35/35) | 200000 | 30 | 5 | 18 |
| 36 | Rf (OH) maleate/MA/EMA (30/35/35) | 200000 | 30 | 5 | 18 |
| 37 | Rf (OH) maleate/MMA/CHMA (30/35/35) | 150000 | 30 | 6 | 17 |
| 38 | Rf (OH) maleate/MMA/EMA/CHMA (30/30/30/10) | 180000 | 30 | 6 | 16 |
| 39 | [Rf (OH) maleate/MMA/EMA/Sty (70/12.5/12.5/5) + P-MMA/EMA (80/20)] (50 + 50) | 400000 | 30 | 6 | 15 |
| 40 | [Rf (OH) maleate/MMA/EMA/Sty (30/30/30/10) + Water and oil repellent] (90 + 10) | 400000 | 40 | 5 | 17 |
| 41 | BrRf maleate/MMA/EMA/Sty (30/30/30/10) | 100000 | 20 | 5 | 18 |
| 42 | BrRf (OH) maleate/MMA/EMA/Sty (30/30/30/10) | 100000 | 30 | 6 | 15 |
| 43 | BrRf fumarate/MMA/EMA/Sty (30/30/30/10) | 200000 | 20 | 4 | 22 |

TABLE I-continued

| | | | | | |
|---|---|---|---|---|---|
| 44 | BrRf (OH) fumarate/ MMA/EMA/ Sty (30/30/30/10) | 200000 | 20 | 5 | 18 |
| 45 | $C_8F_{17}SA$ maleate/MMA/EMA/ Sty (30/30/30/10) | 200000 | 20 | 5 | 18 |
| 46 | $C_8F_{17}SA$ fumarate/MMA/EMA/ Sty (30/30/30/10) | 300000 | 20 | 4 | 22 |
| 47 | Rf maleate/MMA | 60000 | 20 | 4 | 25 |
| 48 | $C_8F_{17}SA$ (H) maleate/MMA/EMA/Sty | 190000 | 20 | 5 | 18 |

| Comparative Example No. | Composition of polymer (weight ratio) | Water repellency | Oil repellency | Stainproof properties |
|---|---|---|---|---|
| Comparative example 1 | Rf maleate Homopolymer (100) | 20 | 4 | 30 |
| Comparative example 2 | Rf fumarate Homopolymer (100) | 10 | 3 | 32 |
| Comparative example 3 | MeRf maleate Homopolymer (100) | 10 | 1 | 34 |
| Comparative example 4 | MeRf maleate/MMA (70/30) | 0 | 0 | 30 |
| Comparative example 5 | MeRf maleate/Sty (70/30) | 0 | 0 | 29 |
| Comparative example 6 | MeRf maleate/MMA/Sty (70/15/15) | 0 | 1 | 29 |
| Comparative example 7 | MeRf maleate/MMA (30/70) | 0 | 0 | 28 |
| Comparative example 8 | MeRf maleate/Sty (30/70) | 0 | 0 | 28 |
| Comparative example 9 | MeRf maleate/MMA/Sty (70/15/15) | 10 | 1 | 30 |
| Comparative example 10 | $MeC_8F_{17}SA$ maleate Homopolymer (100) | 10 | 1 | 30 |
| Comparative example 11 | $MeC_8F_{17}SA$ maleate/MMA (30/70) | 0 | 0 | 28 |
| Comparative example 12 | $iPrC_8F_{17}$ fumarate/VPiv (90/10) | 20 | 1 | 30 |
| Comparative example 13 | Rf itaconate/MMA (30/70) | 20 | 2 | 27 |
| Comparative example 14 | $MeC_8F_{17}SA$ maleate/$C_8F_{17}SA$ maleate/MMA (21/9/70) | 0 | 0 | 28 |
| Comparative example 15 | $BuC_8F_{17}SA$ maleate/VAc (68/32) | 0 | 0 | 31 |
| Comparative example 16 | $EtC_8F_{17}SA$ maleate/VPr/GMA (78/20/2) | 0 | 0 | 31 |

Note)

Rf maleate:

(Mixture wherein a molar ratio of $C_6F_{13}$, $C_8F_{17}$, $C_{10}F_{21}$, $C_{12}F_{25}$ and $C_{14}F_{29}$ (=Rf) is 2:50:30:15:3)

Rf fumarate:

(Mixture wherein a molar ratio of $C_6F_{13}$, $C_8F_{17}$, $C_{10}F_{21}$, $C_{12}F_{25}$ and $C_{14}F_{29}$ (=Rf) is 2:50:30:15:3)

Rf(OH) maleate:

(Mixture wherein a molar ratio of $C_6F_{13}$, $C_8F_{17}$, $C_{10}F_{21}$, $C_{12}F_{25}$ and $C_{14}F_{29}$ (=Rf) is 2:50:30:15:3)

Rf(OH) fumarate:

(Mixture wherein a molar ratio of $C_6F_{13}$, $C_8F_{17}$, $C_{10}F_{21}$, $C_{12}F_{25}$ and $C_{14}F_{29}$ (=Rf) is 2:50:30:15:3)

MMA: Methyl methacrylate
Sty: Styrene
EMA: Ethyl methacrylate
BMA: Butyl methacrylate
StA: Stearyl acrylate
MA: Methyl acrylate
EA: Ethyl acrylate
CHMA: Cyclohexyl methacrylate
Water and oil repellent: TG-452A (manufactured by Daikin Industries Ltd.)

BrRf maleate:

(Mixture wherein a molar ratio of $C_7F_{15}$, $C_9F_{19}$, $C_{11}F_{23}$, $C_{13}F_{27}$ and $C_{15}F_{31}$ (=Rf) is 2:50:30:15:3)

BrRf fumarate:

(Mixture wherein a molar ratio of $C_7F_{15}$, $C_9F_{19}$, $C_{11}F_{23}$, $C_{13}F_{27}$ and $C_{15}F_{31}$ (=Rf) is 2:50:30:15:3)

BrRf(OH) maleate:

(Mixture wherein a molar ratio of $C_7F_{15}$, $C_9F_{19}$, $C_{11}F_{23}$, $C_{13}F_{27}$ and $C_{15}F_{31}$ (=Rf) is 2:50:30:15:3)

BrRf(OH) fumarate:

(Mixture wherein a molar ratio of $C_7F_{15}$, $C_9F_{19}$, $C_{11}F_{23}$, $C_{13}F_{27}$ and $C_{15}F_{31}$ (=Rf) is 2:50:30:15:3)

$C_8F_{17}SA$ maleate:

$C_8F_{17}SA$ fumarate: Trans-form of $C_8F_{17}SA$ maleate $C_8F_{17}SA(H)$ maleate:

MeRf maleate:

(Mixture wherein a molar ratio of $C_6F_{17}$, $C_8F_{17}$, $C_{10}F_{21}$, $C_{12}F_{25}$ and $C_{14}F_{29}$ (=Rf) is 2:50:30:15:3)

MeC$_8$F$_{17}$SA maleate:

iPrC$_8$F$_{17}$ fumarate:

VPiv: Vinyl pivalate
Rf itaconate:

BuC$_8$F$_{17}$SA maleate:

VAc: Vinyl acetate
EtC$_8$F$_{17}$SA maleate:

VPr: Vinyl propionate
GMA: Glycidyl methacrylate

EFFECT OF THE INVENTION

The stainproofing agent of the present has excellent water repellency, oil repellency and stainproof properties which have never been heretofore obtained.

We claim:

1. A stainproofing agent comprising a fluorine-containing copolymer, said fluorine-containing copolymer comprising:

(A) at least one repeating unit derived from a monomer which is selected from the group consisting of an OH—and fluorine-containing maleate represented by the formula:

wherein Rf is a perfluoroalkyl group having 3 to 21 carbon atoms, an OH—and fluorine-containing fumarate represented by the formula:

wherein Rf is a perfluoroalkyl group having 3 to 21 carbon atoms, a fluorine-containing maleate represented by the formula:

wherein Rf is a perfluoroalkyl group having 3 to 21 carbon atoms, and A is an alkylene group having 1 to 4 carbon atoms or wherein $R^1$ is a hydrogen atom or an alkyl group having 1 to 4 carbon atoms, and $R^2$ is an alkylene group having 1 to 4 carbon atoms, and a fluorine-containing fumarate represented by the formula:

wherein Rf is a perfluoroalkyl group having 3 to 21 carbon atoms, and A is an alkylene group having 1 to 4 carbon atoms or wherein $R^1$ is a hydrogen atom or an alkyl group having 1 to 4 carbon atoms, and $R^2$ is an alkylene group having 1 to 4 carbon atoms; and

(B) at least one repeating unit derived from an alkyl (meth)acrylate whose alkyl group has 1 to 6 carbon atoms.

2. A stainproofing agent comprising a fluorine-containing copolymer, said fluorine-containing copolymer comprising:

(A) at least one repeating unit derived from an OH— and fluorine-containing maleate represented by the formula:

wherein Rf is a perfluoroalkyl group having 3 to 21 carbon atoms, or a fluorine-containing maleate represented by the formula:

wherein Rf is a perfluoroalkyl group having 3 to 21 carbon atoms, and A is an alkylene group having 1 to 4 carbon atoms or wherein $R^1$ is a hydrogen atom or an alkyl group having 1 to 4 carbon atoms, and $R^2$ is an alkylene group having 1 to 4 carbon atoms, (B) at least one repeating unit derived from an alkyl (meth)acrylate whose alkyl group has 1 to 6 carbon atoms, and

(C) a repeating unit derived from styrene.

3. A stainproofing agent comprising an OH— and fluorine-containing copolymer, said fluorine-containing copolymer comprising:

(A) at least one repeating unit derived from an OH— and fluorine- containing fumarate represented by the formula:

wherein Rf is a perfluoroalkyl group having 3 to 21 carbon atoms, or a fluorine-containing fumarate represented by the formula:

wherein Rf is a perfluoroalkyl group having 3 to 21 carbon atoms, and A is an alkylene group having 1 to 4 carbon atoms or wherein $R^1$ is a hydrogen atom or an alkyl group having 1 to 4 carbon atoms, and $R^2$ is an alkylene group having 1 to 4 carbon atoms, (B) at least one repeating unit derived from an alkyl (meth)acrylate whose alkyl group has 1 to 6 carbon atoms; and

(C) a repeating unit derived from styrene.

4. A stainproofing agent comprising a fluorine-containing copolymer, said fluorine-containing copolymer comprising:

(A) at least one repeating unit derived from a monomer which is selected from an OH— and fluorine-containing maleate represented by the formula:

wherein Rf is a perfluoroalkyl group having 3 to 21 carbon atoms, an OH— and fluorine-containing fumarate represented by the formula:

wherein Rf is a perfluoroalkyl group having 3 to 21 carbon atoms, a fluorine-containing maleate represented by the formula:

wherein Rf is a perfluoroalkyl group having 3 to 21 carbon atoms, and A is an alkylene group having 1 to 4 carbon atoms or wherein $R^1$ is a hydrogen atom or an alkyl group having 1 to 4 carbon atoms, and $R^2$ is an alkylene group having 1 to 4 carbon atoms, or a fluorine-containing fumarate represented by the formula:

wherein Rf is a perfluoroalkyl group having 3 to 21 carbon atoms, and A is an alkylene group having 1 to 4 carbon atoms or wherein $R^1$ is a hydrogen atom or an alkyl group having 1 to 4 carbon atoms, and $R^2$ is an alkylene group having 1 to 4 carbon atoms,

(B) two repeating units derived from an alkyl (meth)acrylate whose alkyl group has 1 to 6 carbon atoms, and (C) a repeating unit derived from styrene.

5. The stainproofing agent according to any one of claims 1 to 4, wherein the repeating unit (A) is derived from an OH—and fluorine-containing maleate represented by the formula:

wherein Rf is a perfluoroalkyl group having 3 to 21 carbon atoms, or an OH—and fluorine-containing fumarate represented by the formula:

wherein Rf is a perfluoroalkyl group having 3 to 21 carbon atoms.

6. The stainproofing agent according to claim 1, the repeating unit (B) is derived from an alkyl (meth)acrylate whose alkyl group has 1 to 3 carbon atoms.

* * * * *